(12) United States Patent
Levin

(10) Patent No.: US 6,384,294 B1
(45) Date of Patent: May 7, 2002

(54) PROTECTIVE BANDAGES INCLUDING FORCE-TRANSMISSION-IMPEDING MEMBERS THEREIN

(76) Inventor: John M. Levin, 412 Fairview Ave., Narberth, PA (US) 19072

( * ) Notice: Subject to any disclaimer, the term of this patent is extended or adjusted under 35 U.S.C. 154(b) by 0 days.

(21) Appl. No.: 09/615,211

(22) Filed: Jul. 13, 2000

(51) Int. Cl.$^7$ ................................................ A61F 13/00
(52) U.S. Cl. ........................... 602/41; 602/42; 602/43; 602/44; 602/45; 602/46; 602/47
(58) Field of Search ..................................... 602/41–47

(56) References Cited

U.S. PATENT DOCUMENTS

| | | |
|---|---|---|
| 1,913,928 A | 6/1933 | Kaufman |
| 2,443,140 A | 6/1948 | Larsen |
| 2,992,644 A | 7/1961 | Plantinga et al. |
| 3,171,410 A | 3/1965 | Towle, Jr. et al. |
| 3,416,525 A | 12/1968 | Yeremian |
| 3,927,669 A | 12/1975 | Glatt |
| 4,023,569 A | 5/1977 | Warnecke et al. |
| 4,224,945 A | 9/1980 | Cohen |
| 4,285,338 A | 8/1981 | Lemelson |
| 4,561,435 A | 12/1985 | McKnight et al. |
| 4,616,644 A | 10/1986 | Saferstein et al. |
| 4,962,769 A | 10/1990 | Garcia |
| 4,964,858 A | 10/1990 | Livny |
| 5,170,781 A | 12/1992 | Loomis |
| 5,330,452 A * | 7/1994 | Zook ........................... 604/307 |
| 5,336,209 A | 8/1994 | Porzilli |
| 5,438,984 A * | 8/1995 | Schoendorfer .............. 128/632 |
| 5,954,679 A | 9/1999 | Baranitsky |

* cited by examiner

Primary Examiner—Michael A. Brown
Assistant Examiner—Lalita M. Hamilton
(74) Attorney, Agent, or Firm—Caesar, Rivise, Bernstein, Cohen & Pokotilow, Ltd.

(57) ABSTRACT

Protective bandages in accordance with this invention include an anchoring strip having a protective layer on a lower surface thereof for overlying a desired area on a person's skin. Force-transmission-impeding means is provided on the side of the anchoring strip opposed to the side including the protective layer. The force-transmission-impeding means includes a top sheet adhered adjacent peripheral edges thereof to an upper surface of the anchoring strip to define an internal compartment between the anchoring strip and the top sheet. A compressive cushioning member is provided within the internal compartment for absorbing compressive forces, and low friction, relatively movable confronting surfaces are provided within the internal compartment spaced from the upper surface of the anchoring strip to absorb shear forces imposed upon the bandage. In certain embodiments of this invention, two pairs of low friction, relatively movable confronting surfaces are provided, whereas in another embodiment of this invention only one pair of low friction, relatively movable confronting surfaces is provided.

37 Claims, 4 Drawing Sheets

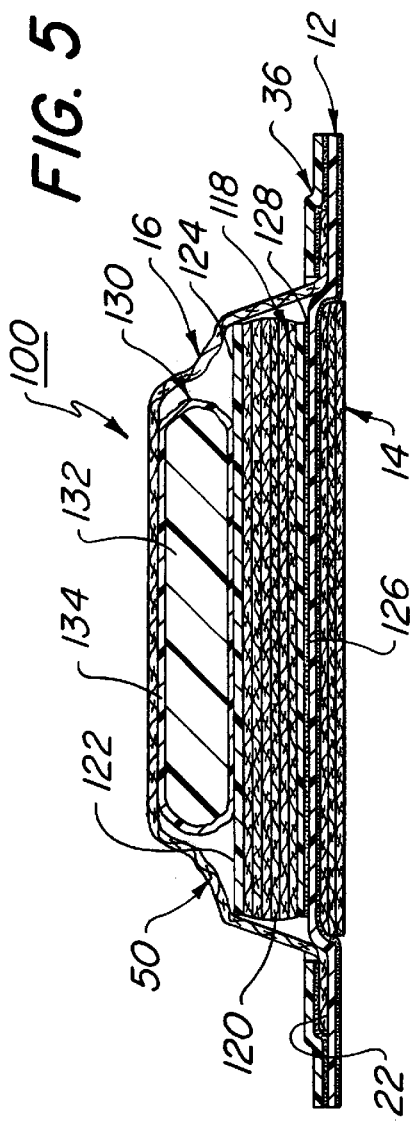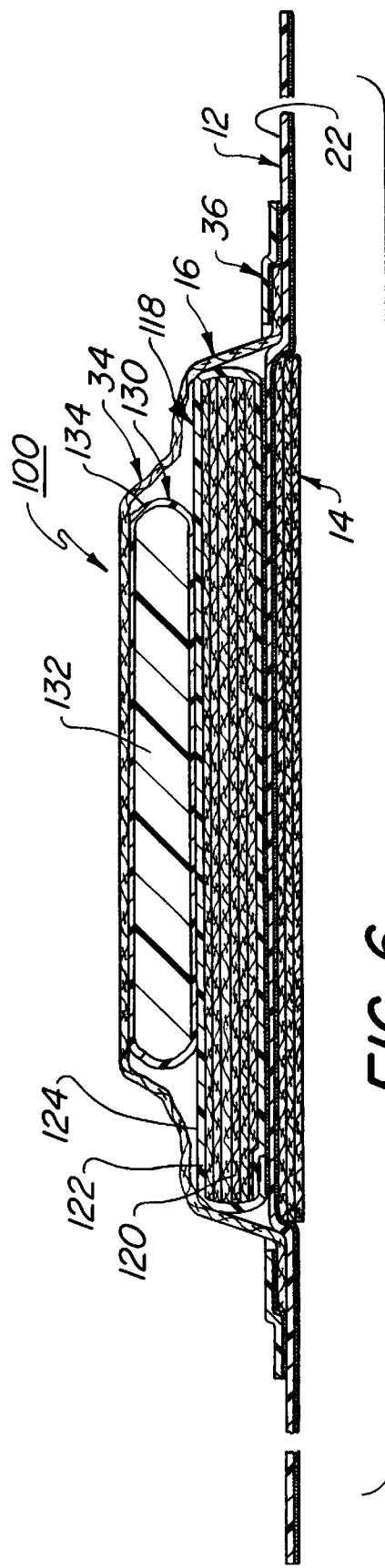

PROTECTIVE BANDAGES INCLUDING FORCE-TRANSMISSION-IMPEDING MEMBERS THEREIN

FIELD OF THE INVENTION

This invention relates generally to protective bandages, and more particularly to protective bandages including force-transmission-impeding members therein.

BACKGROUND OF THE INVENTION

Protective bandages are used for a wide variety of applications, including the protection of skin grafts, surgical wounds, traumatic wounds e.g., cuts and abrasions, decubitus ulcers (or prevention thereof) that most commonly form in areas of the sacral, hip, buttocks and elbows. These protective bandages come in a variety of sizes to protect injured skin areas of varying sizes. For example, bandages having a length in the range of 1" to 2" generally are provided to protect blisters and similar skin injuries. Bandages that are generally 3" to 4" in length are commonly employed to protect small surgical incisions of the type that are made in hernia operations and in other minor surgical procedures. Bandages that are 6" to 8" in length, and even longer, are employed to protect larger incisions that are made in connection with major surgical procedures, e.g., back surgery and heart related surgeries. Bandages employed to protect surgical incisions generally are in the range of 2" to 3" wide.

Common prior art protective bandages generally include an inner gauze or other protective layer or member surrounded by an adhesive layer. The gauze or other protective member is placed over the area of the skin to be protected, and is adhered in that position by the sounding adhesive layer. While these bandages do protect the injured skin area from direct external contact with other surfaces, forces imposed on the bandage, either compressive or shear, often are transmitted to the inner protective layer and to the underlying injured area. Thus, when an external force is applied to the outer surface of the bandage, that force often is transmitted to the injured area, thereby either re-injuring the area or preventing the area from healing properly.

Although bandages for absorbing forces are disclosed in the prior art, a need exists for improved structures that are more effective in shielding an injured area on a person's skin from external forces, both compressive and shear.

U.S. Pat. No. 1,913,928, issued to Kauffman, discloses a device for treating and protecting corns. In this device, a sac-like, hollow-walled body is separated by a space including air or another buoyant fluid therein, such as glycerin. Although the patentee states that the sac-like body has inherent elastic qualities, it is not employed in connection with a protective bandage of the type forming the subject matter of the present invention. In fact, the sac-like member is placed in direct contact with a person's skin; preferably behind an area to be protected. In other words, in a preferred mode of the invention the protective member is not placed directly over an area to be protected.

Moreover, the sac-like arrangement disclosed in the Kauffman '928 patent is not believed to be optimum for isolating the skin surface contacted by the sac-like member from shear forces.

U.S. Pat. No. 5,170,781, issued to Loomis, discloses several embodiments of a protective bandage. In the embodiments illustrated in FIGS. 1–4, a bubble-type member 120 (or multiple bubbles 120A) filled with air are positioned on the upper surface of a bandage to purportedly provide a cushioning effect. The patentee states that the protective bubbles(s) is (are) filled with air and are disposed only over the region of the bandage including the sterile pad. Although the Loomis construction may be effective to protect a wound against compressive forces, shear forces imposed upon the upper surface of the bandage still will be undesirably transmitted through the bandage to an underlying area of the skin in contact with the protective gauze pad of said bandage.

U.S. Pat. No. 5,945,679, issued to Baranitsky, describes an adhesive bandage construction that is intended to dissipate frictional (i.e., shear) forces imposed upon the outer surface of the bandage prior to those forces being transmitted to a protective pad 28. In this construction. the bandage includes a conventional anchoring member 12 that extends beyond sterile pad 28 to provide wings having an adhesive material thereon to thereby adhere the bandage to a person's skin in a conventional manner. In the disclosed structure, a flexible planar body or sheet 20 is positioned the lower side of the bandage between the anchoring member and the sterile pad to purportedly preclude shear forces imposed upon the anchoring member from being transmitted to the sterile pad. In this construction, the planar sheet 20 is adhered to the anchoring member 12 at the peripheral edges thereof and remains unconnected to the anchoring member over substantially the entire inner surface of the planar sheet material. In view of the fact that the planar sheet material 20 is physically connected to the anchoring member, any shear force imposed upon the anchoring member will be transmitted to the planar sheet 20, thereby inherently imparting some shear force to the underlying sterile pad 28.

In view of the deficiencies existing with prior art bandages, a need exists for protective bandages of the type that effectively protect the wound from external forces imposed upon the bandage, e.g., compressive forces and/or shear forces.

A particularly acute problem exists in connection with the protection of decubitus ulcers or the prevention thereof, as well as the protection of skin grafts. Skin grafts are very slippery when initially applied, and tend to shift if the protective layer of a bandage in contact with the graft is caused to shift as a result of experiencing an external shear force applied to an outer surface of the bandage. In other words, skin grafts often experience movement regardless of the best efforts employed to attempt to immobilize them.

There is a definite need for a protective bandage having particular benefit in protecting skin grafts and also in protecting or preventing the formation of decubitus ulcers. It is to such a bandage that the present invention relates.

OBJECTS OF THE INVENTION

It is a general object of this invention to provide protective bandages that impede the transmission of external forces from the outer surface of the bandage to inner surfaces engaging an injured area of the skin to be protected.

It is a more specific object of this invention to provide protective bandages that impede the transmission of external compressive and shear forces from the outer surface of the bandage to inner surfaces engaging an injured area of the skin to be protected.

It is still a further object of this invention to provide a protective bandage for protecting a variety of skin conditions.

It is a more specific object of this invention to provide a protective bandage having desirable properties for protecting skin grafts.

It is yet another specific object of this invention to provide a protective bandage having desirable properties for protecting or preventing the formation of decubitus ulcers.

It is still a further object of this invention to provide a protective bandage that prevent the undesired transmission of moisture e.g., sweat and urine, from permeating into the region of the protective layer contacting the skin, and also to absorb moisture or exudate directed through the bandage from a wounded area of a person's skin.

SUMMARY OF THE INVENTION

The above and other objects of this invention are achieved in a protective bandage of the type including an anchoring strip having a protective layer on a lower surface thereof for overlying a desired area on a person's skin and also including an adhesive on the lower surface for attaching the bandage to the person's skin, said bandage including force-transmission-impeding means disposed above the anchoring strip.

In accordance with this invention, a top sheet is adhered adjacent peripheral edges thereof to an upper surface of the anchoring strip to define an internal compartment between the anchoring strip and the top sheet. A compressive, cushioning member is retained within the internal compartment for absorbing compressive forces, and low friction, relatively movable, contiguous surfaces within the internal compartment are spaced from the upper surface of the anchoring strip and are capable of sliding relative to each other to absorb shears, or lateral, forces imposed upon the bandage.

In a preferred embodiment of this invention, the top sheet is a planar mesh fabric that is stretchable in all directions within the plane of the fabric, to thereby stretch under the influence of shear forces imposed upon the fabric.

In the preferred form of this invention, the compressive cushioning member includes a gel-type material having at least some ability to maintain its shape when unexposed to external forces. A preferred gel-type material usable in this invention is sold commercially under the name "GAK" and has gel-like properties permitting it to move under the influence of both shear and compressive forces.

In accordance with one embodiment of this invention, the low friction, relatively movable confronting surfaces include the inner surface of the top sheet and an upper surface of the compressive cushioning member. When the compressive cushioning member includes "GAK" or other gel-type material, it is often desirable to additionally include an outer layer made of thin plastic film or other low friction material, to thereby provide the low friction surface for cooperating with the low friction lower surface of the top sheet.

In a more preferred embodiment of this invention, the force-transmission-impeding means includes, in addition to a first compressive, cushioning member, an additional member that is freely movable within the internal compartment provided between the top sheet and the anchoring strip. Specifically, this additional member is a free-floating member positioned between the top sheet and an upper, low friction surface of the first compressive cushioning member, and is free to move in all directions within the internal compartment under the influence of external shear forces imposed upon the upper surface of the bandage.

In a preferred embodiment of this invention, the additional member can also be provided with cushioning or compressive materials; provided that outer planar surfaces thereof are of a low friction material to permit easy sliding movement between the additional member and the inner surface of the top sheet and the upper, low friction surface of the first compressive member. In this preferred embodiment, there are two planes in which relative sliding movement takes place to dissipate shear forces. The first plane is between the inner surface of the top sheet and the upper surface of the additional, freely movable member. The second plane is between the additional freely movable member and the upper, low friction surface of the first cushioning member. Moreover, when the additional cushioning member includes compressive material therein, it will cooperate with the first compressive cushioning member to enhance, or provide additional cushioning against normal forces imposed upon the bandage.

BRIEF DESCRIPTION OF THE DRAWINGS

Other objects and many attendant features of this invention will become readily appreciated as the same becomes better understood by reference to the following detailed description when considered in connection with the accompanying drawings wherein:

FIG. 5 is an enlarged sectional view similar to FIG. 2, showing an alternate embodiment of this invention;

FIG. 6 is an enlarged sectional view similar to FIG. 3, showing the embodiment illustrated in FIG. 5.

DESCRIPTION OF THE PREFERRED EMBODIMENTS OF THE INVENTION

It should be understood that the anchoring strip 12, the protective layer 14 and the adhesive for securing the anchoring strip to a person's skin can all be of a conventional design, and do not form any limitation on the present invention. For example, the anchoring strip 12 can be made of any suitable plastic or fabric material. The protective layer 14 can be made of gauze, absorbent plastic, etc. Any other arrangement of an anchoring strip and protective layer is considered to be within the scope of the present invention.

It should be understood that the anchoring strip 12, the protective layer 14 and the adhesive for securing the anchoring strip to a person's skin can all be of a conventional design, and do not form any limitation on the present invention. For example, the anchoring strip 12 can be made of any suitable plastic or fabric material. The sterile pad 28 can be made of gauze, absorbent plastic, etc. Any other arrangement of an anchoring strip and protective layer is considered to be within the scope of the present invention.

Figure 2:
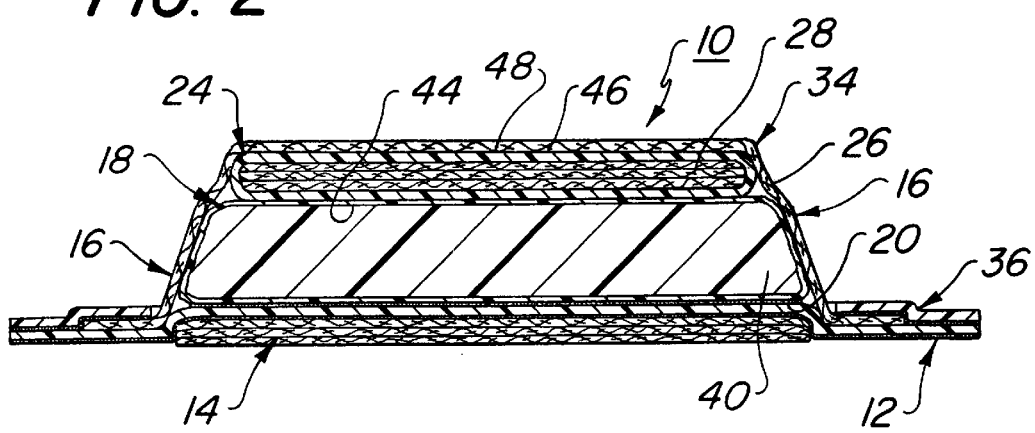
FIG. 2 is an enlarged sectional view taken along line 2—2 of FIG. 1.
Figure 3:
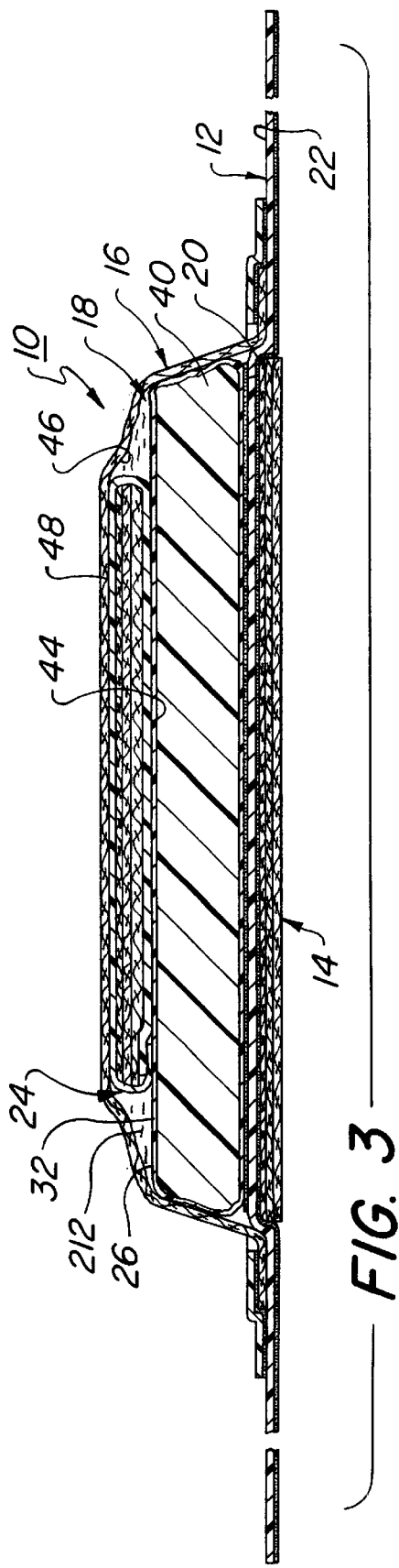
FIG. 3 is an enlarged sectional view taken along line 3—3 of FIG. 1.
Figure 4:
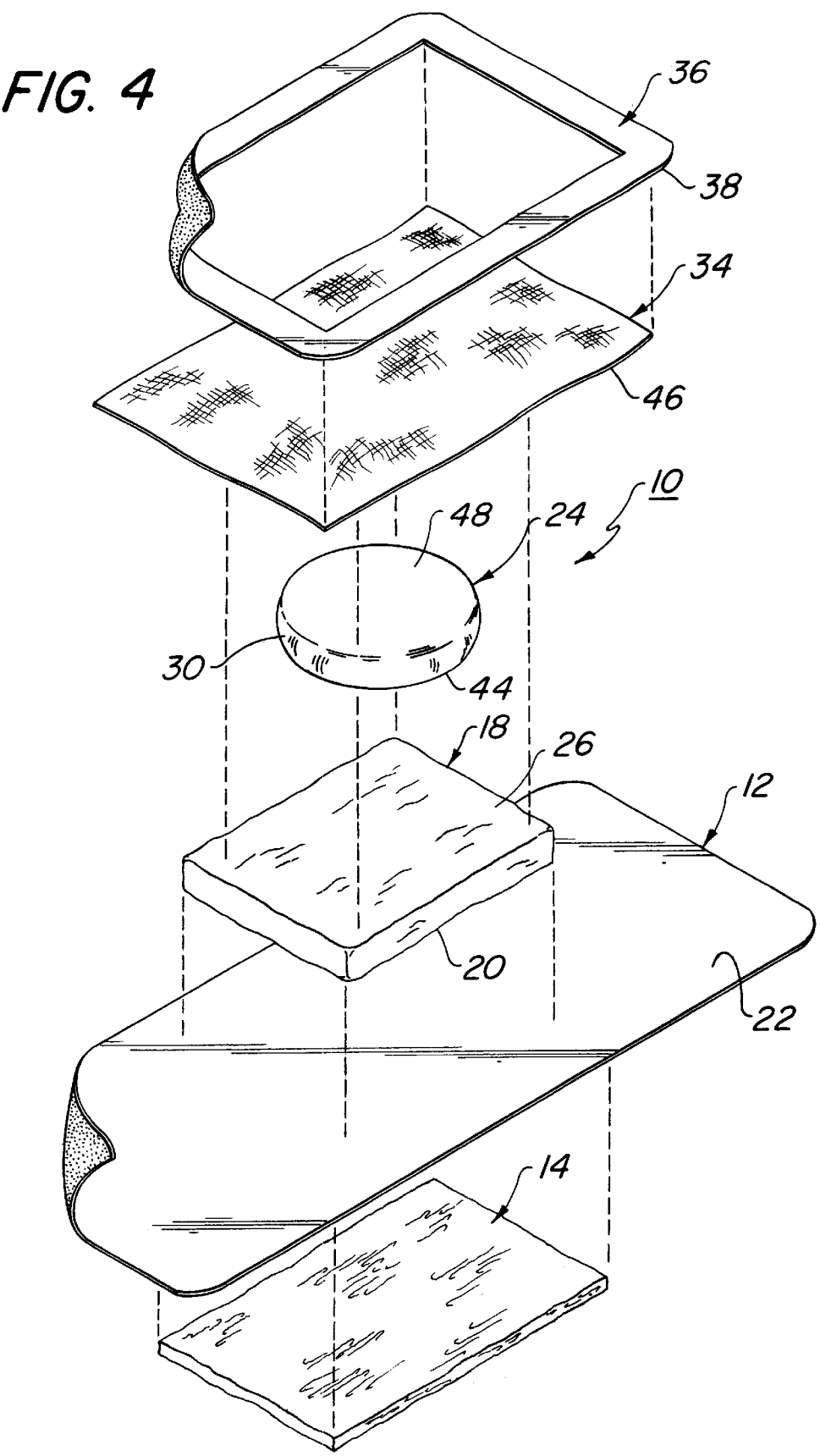
FIG. 4 is an exploded isometric view of the bandage shown in FIG. 1 to more clearly illustrate the component parts thereof.

Turning specifically to FIGS. 2 through 4, the upper construction 16 includes a lower compressive cushioning member 18 having a lower surface 20 adhered through a suitable adhesive to upper surface 22 of the anchoring strip 12 to prevent relative sliding movement between the cushioning member and the anchoring strip. Immediately above the lower compressive cushioning member 18 and in contact therewith is a generally pancake-like compressive disc 24 positioned on upper surface 26 of the lower compressive cushioning member 18 and being of a smaller dimension then the cushioning member so as to be freely slidable in all directions on said upper surface 26.

This compressive disc 24 preferably is round or oval, including curved peripheral edges so as to eliminate sharply defined peripheral edge surfaces that could impede the ability of the disc to slide freely on the upper surface 26 of the compressive cushioning member 18.

In the illustrated embodiment, the compressive disc 24 includes an internal compressive section 28 that can include any desired compressive material such as sheets of tissue, gauze, gel-like material and the like. In addition, the compressive disc 24 includes an outer, low-frictioned covering member 30, which can be in the form of a thin plastic film, such as polypropylene, polyethylene or the like, provided that it has a relatively low friction surface for permitting the compressive disc 24 to freely slide in all directions on the upper surface 26 of the compressive cushioning member 18 when exposed to externally-imposed shear forces. It should be noted that the upper surface 26 of the cushioning member 18 likewise is a surface of a low-friction material, such as a surface of an outer wrap of plastic film 32, made from polypropylene, polyethylene or the like. In fact, in the preferred construction, the lowest frictional resistance to sliding movement in the bandage takes place between the compressive disc 24 and the compressive cushioning member 18.

As noted above, in order to permit the compressive disc 24 to freely slide relative to the cushioning member 18, it is constructed of smaller planar dimensions than the cushioning member 18 and is free of sharply defined edge surfaces. This arrangement can be seen best in FIGS. 2 and 3.

Still referring to FIG. 4, a planar top sheet 34, which preferably has elastic properties in all directions within its plane, is positioned over the compressive disc 24 and its peripheral edges thereof are secured directly to the upper surface 22 of the anchoring strip 12 by a perimeter strip 36 having adhesive on the lower surface 38 thereof. The perimeter strip 36 can be made of the same material as the anchoring strip 12, so as to provide an aesthetically pleasing surface appearance to the construction.

The elastic top sheet 34 can be made of any desired elastic material that is capable of elastically stretching in all planar directions under the influence of shear forces. For example, a nylon mesh fabric of a weave commonly employed in women's nylon stockings is suitable for use in this invention. The desired thickness of the top sheet 34 can be easily determined by a person skilled in the art based upon the shear forces that will be encountered during use of the bandage 10, and the nature of the internal components on the upper construction 16.

Turning specifically to FIGS. 2 and 3, the lower compressive cushioning member 18 most preferably includes a gel-type material 40 that essentially maintains its shape unless directly exposed to external forces. The gel-type material is capable of moving when exposed to shear or compressive forces to aid in talking up these forces prior to their transmission to the protective layer 14 and underlying protective area of the skin.

In a preferred embodiment of this invention, the gel-type material can be a material sold under the name "GAK". As noted above, in accordance with a preferred embodiment of this invention, the "GAK" or other gel-type material is enclosed within an outer, low friction wrap of plastic film 32 and then adhered through an adhesive layer 42 to the upper surface 22 of the anchoring strip 12. This prevents relative sliding movement between the cushioning member 18, and the anchoring strip 12.

Figure 1:
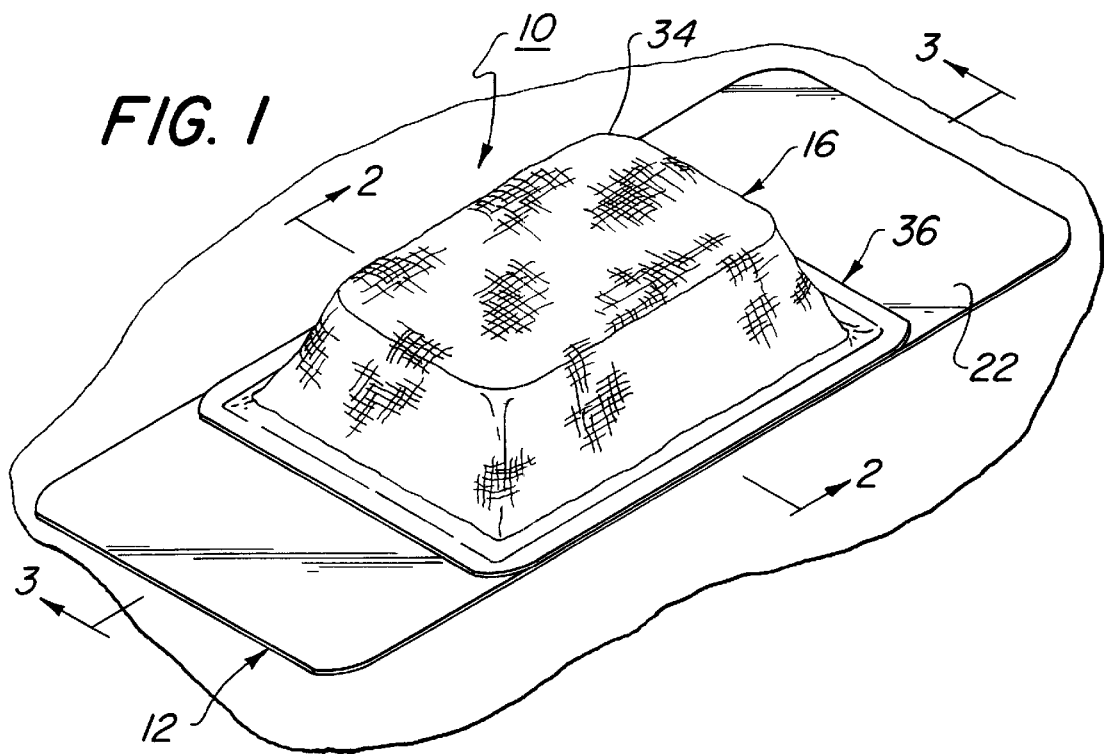
FIG. 1 is an enlarged isometric view of a first embodiment of a bandage in accordance with this invention.

Referring to FIGS. 1–3, it should be noted that the top sheet 34 provides the entire outer surface of the upper construction 16; completely confining the cushioning member 18 and the compressive disc 24 within the internal compartment provided between the anchoring strip 12 and the top sheet 34. It should be understood that, although the top sheet 34 is illustrated as being in close conformity with the members within the internal compartment, the top sheet 34 can be adhered to the upper surface 22 of the anchoring strip 12 with some slack.

The construction of the bandage 10 provides a unique cooperation of elements that has not been achieved in prior art constructions. Specifically, in the bandage 10 shear forces are taken up by the relative sliding movement of contiguous surfaces that are spaced outwardly from the upper surface 22 of the anchoring strip 12. In particular, in the preferred construction of this invention, relative sliding movement takes place between the upper surface 26 of the cushioning member 18 and the contiguous surface 44 of the compressive disc 24. As noted above, the least resistance to sliding movement takes place between these latter two surfaces. In addition, relative sliding movement can take place between the inner surface 46 of the top sheet 34 and the contiguous tipper surface 48 of the compressive disc 24. In the preferred embodiments of the invention there is somewhat greater resistance to sliding movement between the top sheet 34 and the compressive disc 24 than between the compressive disc 24 and the compressive cushioning member 18. Thus, in the preferred embodiment of this invention, there are two pairs of contiguous surfaces that are capable of moving relative to each other to absorb shear forces imposed upon the bandage, and both of these pairs of surfaces are disposed outwardly of the upper surface 22 of the anchoring strip 12. This arrangement should effectively result in the dissipation of shear forces imposed upon the bandage prior to those shear forces being imposed upon the protective layer 14 engaging a protected area of a person's skin.

It also should be noted that at least a portion of the shear forces imposed on the top sheet 34 can be dissipated by the stretching of the top sheet or by relative sliding movement between the outer surface of the top sheet and the member or surface imposing the shear force thereon. However, in the preferred embodiments of this invention it is expected that the shear forces will be predominately dissipated by the sliding movement between the compressive disc 24 and the compressive member 18, and the sliding movement between the compressive disc 24 and the top sheet 34.

In addition, it should be noted that the use of a gel-type material 40 in the cushioning member 18 provides several functions. First, the gel-type material has excellent cushioning properties, to thereby protect an underlying skin area from compressive forces. In addition, the gel-type material is capable of laterally extending or stretching, such as a gelatin sold under the trademark Jell-O, to thereby also assist in taking up shear forces, if needed.

By physically attaching the compressive cushioning member 18 to the upper surface 22 of the anchoring strip 12, any shear forces imposed upon the bandage 10 will tend to be dissipated by the relative sliding movement between the compressive disc 24 and both the lower compressive cushioning member 18 and the top sheet 34, since these are the lowest friction sections of the bandage.

Referring to FIGS. 5 and 6, a second embodiment of a protective bandage in accordance with this invention is shown at 100. As in the first embodiment of this invention, the protective bandage 100 includes an anchoring strip 12, a protective layer 14 in the form of a sterile pad disposed in the central region of the anchoring strip and an adhesive layer surrounding the protective layer to attach the bandage to a person's skin.

Also, as in the construction of the bandage 10, the protective bandage 100 includes a top sheet 34 adhered to upper surface 22 of the anchoring strip 12 by a perimeter strip 36.

The bandage 100 differs from the bandage 10 in the arrangement of the internal components of the upper construction 16 for dissipating both compressive and shear forces. It should be understood that the relative dimensions of the bandage 100 can be varied within the same limits as the bandage 10, and that the sectional views of the bandage 100 illustrated in FIGS. 5 and 6 are comparable to the sectional views shown in FIGS. 2 and 3 with respect to the bandage 10.

Referring specifically to FIGS. 5 and 6, the top sheet 34 cooperates with the upper surface 22 of the anchoring strip 12 to define an internal compartment 50. In this embodiment a lower compressive cushioning member 118 is provided that differs from the compressive cushioning member 18 employed in the bandage 10. Specifically, the lower compressive cushioning member 118 includes a central core 120 in the form of multiple gauze sheets or other desired sheet material. The central core 120 is confined within an outer plastic film layer 122, which can be of the same plastic employed as the outer plastic wrap 32 in the bandage 10. The outer plastic film wrap 122 provides an upper, low friction surface 124 for purposes to be described hereinafter.

It should be noted that the outer plastic film wrap 122 includes a lower surface 126 that is secured by a suitable adhesive layer 128 to the upper surface 22 of the anchoring strip 12. Thus, this adhesive layer 128 immobilizes the compressive cushioning member 118 against sliding movement relative to the anchoring strip 12.

From the above explanation, it should be understood that the compressive cushioning member 118 is intended to provide a similar function to the compressive cushioning member 18 employed in the bandage 10. However, the cushioning effect of the central core 120 in the cushioning member 118 may not be of the same character as with the use of the cushioning member 18, which includes the gel-type material 40 therein.

Still referring to FIGS. 5 and 6, a pancake-like compressive disc 130 is provided on top of the compressive cushioning member 118. This compressive disc 130 can be of the same general dimensions as the compressive disc 24 employed in the bandage 10, so as to permit this compressive disc to slide freely in all directions relative to the compressive cushioning member 118.

As can be seen in FIGS. 5 and 6, the compressive disc 130 includes an internal core 132, which can be of the same gel-type material 40 employed in the bandage 10. Specifically, this gel-type material can be "GAK."

When the internal core 132 is formed of "GAK" or other gel-type material that has relatively high-friction surfaces, the compressive disc 130 is provided with an outer, low-friction wrap, such as a plastic film wrap 134. This plastic film wrap 134 can be of the same material as the outer, low-friction covering member 30 in the compressive disc 24.

The compressive disc 130 functions to take up both shear and compressive forces in a manner similar to the compressive disc 24 employed in the bandage 10. However, the compressive properties of the disc 130 are somewhat better due to the inclusion of the gel-type material in the core, as opposed to the gauze type material employed in the compressive disc 24.

It should be noted that the bandage 100 functions in essentially the same manner to take up shear forces as the bandage 10. In particular, when the bandage 100 is exposed to shear forces, the compressive disc 130 is permitted to slide freely in all directions relative to the inner surface of the top sheet 34 and the upper surface of the outer plastic film wrap 122 of the lower compressive cushioning member 18 to thereby take-up the imposed shear forces. In other words, the relative sliding movement takes place between two pairs of contiguous surfaces, both of which are spaced outwardly from the upper surface 22 of the anchoring strip 12.

Figure 7:
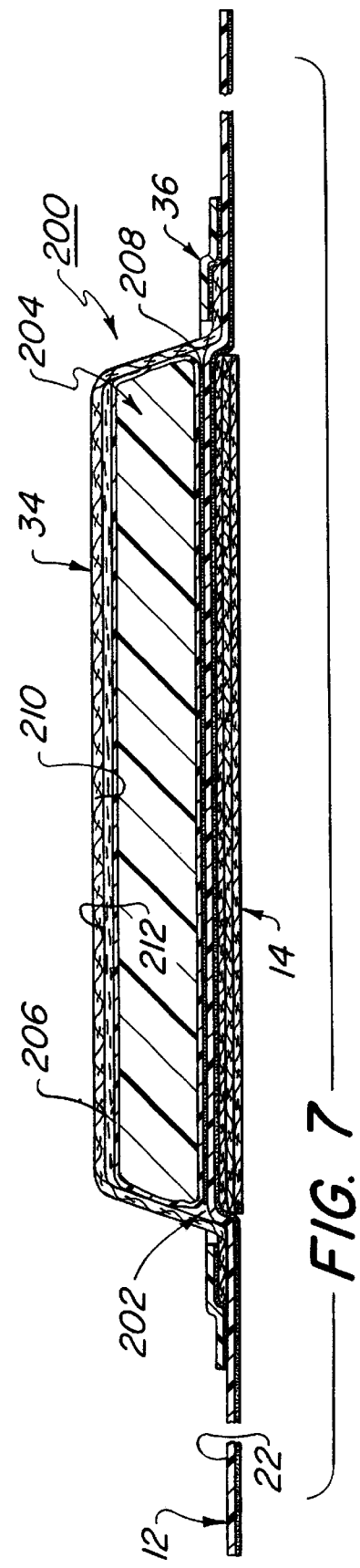
FIG. 7 is an enlarged section view similar to FIG. 3, showing yet another embodiment of this invention.

Referring to FIG. 7, a third embodiment of a protective bandage in accordance with this invention is shown at 200. The protective bandage 200 is of a less preferred construction than the protective bandages 10 and 100, and in particular, does not include any freely movable compressive disc member therein. However, for applications in which the requirements for isolating a protected skin area from shear forces is of a lesser concern, the construction of the protective bandage 200 may be acceptable.

Referring to FIG. 7, the protective bandage 200, like the previously described embodiments, includes an anchoring strip 12, a protective layer 14, a top sheet 34 and a perimeter strip 36 for securing the top sheet 34 to the upper surface 22 of the anchoring strip 12. However, the protective bandage 200 differs from the embodiments of the protective bandages 10 and 100 in that it only includes one member in the interior compartment 202 provided between the top sheet 34 and the anchoring strip 12. That member is a compressive cushioning member 204, which can be of the same construction as the compressive cushioning member 18 in the protective bandage 10. Specifically, the compressive cushioning member 204 can include an internal gel-type core provided with an outer wrap of a low friction plastic sheet material, as is illustrated at 206 in FIG. 7.

An adhesive layer 208 is provided to secure the cushioning member 204 to the upper surface 22 of the anchoring strip 12, thereby immobilizing the cushioning member against sliding movement on the upper surface of the anchoring strip.

In the embodiment illustrated in FIG. 7, the relative sliding movement for taking up undesired shear forces takes place only between inner surface 210 of the top sheet 34 and upper surface 212 of the compressive cushioning member 204. Thus, there is only one pair of surfaces at which relative sliding movement takes place to dissipate shear forces imposed upon the bandage. However, as in the bandage constructions 10 and 100, this pair of sliding surfaces is located above the upper surface 22 of the anchoring strip 12.

It should be noted that in all embodiments of this invention the top sheet 34 preferably is made up of an elastic material that is stretchable in all directions within the plane of the sheet. Thus, any shear forces imposed upon the top sheet 34 will at least be partially taken up by the stretching of the top sheet 34. Moreover, the stretching of the top sheet 34 will take place by the top sheet sliding relative to the contiguous low friction surface of either the compressive disc 24 (bandage 10) the compressive disc 130 (bandage 100), or over the low friction surface of the compressive cushioning member 204 (bandage 200).

If desired, all of the protective bandages within the scope of this invention can be provided with a safe, inert desiccant to absorb moisture. The desiccant can be of any well-known material, such as rice, or a desiccant of the type conventionally used with clothing and other products wherein moisture tends to create a problem.

The desiccant can be included either in the open area in the internal compartment provided between the top sheet 34 and the anchoring strip 12, or, if desired, within the compressive discs 24 or 130 in the protective bandages 10 and 100, respectively. The use of rice as a desiccant is illustrated at 212 in the bandage 10 (FIG. 3).

In many applications, it is highly desirable to prevent moisture, such as sweat and urine exuded by a patient wearing the bandage, from permeating into the region of the protective layer 14 contacting the patient's skin. When the anchoring strip 12 is of an impervious construction, the use of a desiccant may not be necessary. However, for some applications it may be desirable to include a porous anchoring strip into the construction to permit exudate from the wound to pass through the anchoring strip in the internal compartment provided between the anchoring strip and the top sheet 34. In these embodiments, use of a desiccant to help absorb fluids is highly desirable.

It should be understood that applicant has described the preferred embodiments of his invention; it being understood that, in accordance with the broadest aspects of the invention, a bandage is provided that includes force-transmission-impeding means on the upper surface thereof to absorb or otherwise dissipate shear forces upon the upper surface of the bandage prior to those forces being transmitted to the protective layer 14, wherein such shear forces can further damage or preclude the healing of skin injuries.

Without further elaboration, the foregoing will so fully illustrate my invention that others may, by applying current or future knowledge, readily adapt the same for use under various conditions of service.

What I claim of this invention is:

1. A protective bandage for skin surfaces, said bandage including a anchoring strip having a protective layer on a lower surface thereof for overlying a desired area on a person's skin and a force-transmission-impeding means disposed on the side of the strip opposed to the side including the protective layer, said force-transmission-impeding means including a top sheet adhered adjacent peripheral edges thereof to an upper surface of the anchoring strip to define an internal compartment between said anchoring strip and said top sheet, a compressive cushioning member within the internal compartment for absorbing compressive forces, and low friction, relatively moveable confronting surfaces within said internal compartment spaced from the upper surface of the anchoring strip to adsorb shear forces imposed upon the bandage.

2. The protective bandage of claim 1, wherein the top sheet is a fabric stretchable in all directions within the plane of said fabric.

3. The protective bandage of claim 2, wherein said top sheet includes an inner surface that is one of said relative movable confronting surfaces.

4. The protective bandage of claim 3, wherein said compressive member includes an upper surface that is one of said confronting surfaces.

5. The protective bandage of claim 4, wherein said compressive member is secured to the upper surface of the anchoring strip to prevent relative sliding movement between said compressive member and said anchoring strip.

6. The protective bandage of claim 5, wherein said compressive member includes a gel-type material therein.

7. The protective bandage of claim 5, wherein said compressive member includes a layer of multiple sheets therein.

8. The protective bandage of claim 1, wherein the compressive cushioning member includes a gel-type material.

9. The protective bandage of claim 3, wherein said gel-type material is a non-flowing gel-type material.

10. The protective bandage of claim 1, wherein said top sheet includes an inner surface that is one of said relatively movable confronting surfaces.

11. The protective bandage of claim 10, wherein said compressive member includes an upper surface that is one of said confronting surfaces.

12. The protective bandage of claim 11, wherein said compressive member is secured to the upper surface of the anchoring strip to prevent relative sliding movement between said compressive member and said anchoring strip.

13. The protective bandage of claim 12, wherein said compressive member includes a gel-type material therein.

14. The protective bandage of claim 12, wherein said compressive member includes a layer of multiple sheets therein.

15. The protective bandage of claim 1, including an additional member retained between the compressive cushioning member and the top sheet, said additional member being freely movable within the space between the top sheet and the compressive cushioning member for permitting said additional member to move in all directions within said internal compartment when subjected to shear forces imposed upon the bandage.

16. The protective bandage of claim 15, wherein said additional member has smaller planar dimensions than the compressive cushioning member to thereby permit relative sliding movement of the additional member relative to the underlying compressive cushioning member.

17. The protective bandage of claim 15, wherein said additional member includes compressive material therein and opposed low friction surfaces, one of said opposed low friction surfaces being contiguous to the inner surface of said top sheet and the other of said low friction surfaces being contiguous to an upper low friction surface of said compressive cushioning member, said compressive cushioning member being attached to an upper surface of said anchoring strip to preclude relative sliding movement between said compressive cushioning member and said anchoring strip.

18. The protective bandage of claim 17, wherein said compressive material included in said additional member is a gel.

19. The protective bandage of claim 17, wherein said compressive material included in said additional member is a stack of sheets.

20. The protective bandage of claim 17, wherein said opposed low friction surfaces of said additional member are surfaces of a plastic film.

21. The protective bandage of claim 1, wherein a desiccant is included in a region between the top sheet and the anchoring strip.

22. A protective member for protecting an area of a person's body, said protective member including an anchoring member for overlying a desired area on a person's body, said anchoring member having an inner surface facing the person's body and an opposed, outer surface, a force-transmission-impeding means disposed on the opposed, outer surface of the anchoring member and including a top sheet adhered adjacent peripheral edges thereof to said opposed outer surface of the anchoring member to define an internal compartment between the anchoring member and the top sheet, a compressive cushioning member within the internal compartment for absorbing compressive forces, and low friction, relatively moveable confronting surfaces within said internal compartment spaced from the outer surface of the anchoring member to absorb sheer forces imposed upon the protective member.

23. The protective member of claim 22, wherein the top sheet is a fabric stretchable in all directions within the plane of said fabric.

24. The protective member of claim 23, wherein said top sheet includes an inner surface that is one of said relatively moveable confronting surfaces.

25. The protective member of claim 24, wherein said compressive member includes an upper surface that is one of said confronting surfaces.

26. The protective member of claim 22, wherein the compressive cushioning member includes a gel-type material.

27. The protective member of claim 26, wherein said gel-type material is a non-flowing gel-type material.

28. The protective member of claim 22, wherein said top sheet includes an inner surface that is one of said relatively moveable confronting surfaces.

29. The protective member of claim 28, wherein said compressive member includes an upper surface that is one of said confronting surfaces.

30. The protective member of claim 29, wherein said compressive member is secured to the outer surface of the anchoring member to prevent relative sliding movement between said compressive member and said anchoring member.

31. The protective member of claim 22, including an additional member retained between the compressive cushioning member and the top sheet, said additional member being freely moveable within the space between the top sheet and the compressive cushioning member for permitting said additional member to move in all directions within said internal compartment when subjected to sheer forces imposed upon the protective member.

32. The protective member of claim 31, wherein said additional member has smaller planar dimensions than the compressive cushioning member to thereby permit relative sliding movement of the additional member relative to the underlying compressive cushioning member.

33. The protective member of claim 31, wherein said additional member includes compressive material therein and opposed low friction surfaces, one of said opposed low friction surfaces being contiguous to the inner surface of said top sheet and the other of said low friction surfaces being contiguous to an upper low friction surface of said compressive cushioning member, said compressive cushioning member being attached to an upper surface of said anchoring member to preclude relative sliding movement between said compressive cushioning member and said anchoring member.

34. The protective member of claim 33, wherein said compressive material included in said additional member is a gel.

35. The protective member of claim 33, wherein said compressive material included in said additional member is a stack of sheets.

36. The protective member of claim 33, wherein said opposed low friction surfaces of said additional member are surfaces of a plastic film.

37. The protective member of claim 22, wherein a desiccant is included in a region between the top sheet and the anchoring member.

* * * * *